United States Patent [19]

Guerrero

[11] 3,960,839

[45] June 1, 1976

[54] PROCESS FOR RECOVERING AND ISOLATING SOLASODINE AND GLYCOSIDES THEREOF

[75] Inventor: Milton Guerrero, Quito, Ecuador

[73] Assignee: Escuela Politecnica Nacional, Quito, Ecuador

[22] Filed: June 4, 1974

[21] Appl. No.: 476,278

Related U.S. Application Data

[63] Continuation of Ser. No. 331,004, Feb. 9, 1973, abandoned.

[52] U.S. Cl..................... 260/210.5; 260/239.55 A
[51] Int. Cl.²......................................... C07J 21/00
[58] Field of Search............. 260/239.55 A, 210.5 R

[56] References Cited
UNITED STATES PATENTS 2,408,834  10/1946  Wagner.................... 260/239.55 A
2,791,581  5/1957  Wall et al. ...................... 260/210.5

FOREIGN PATENTS OR APPLICATIONS 1,106,133  3/1968  United Kingdom............. 260/210.5

OTHER PUBLICATIONS

Chem. Abstracts, 60:793f.
Chem. Abstracts, 67:71082x.
Chem. Abstracts, 67:54397m.
Chem. Abstracts, 66:38204v.

*Primary Examiner*—Ethel G. Love

[57] ABSTRACT

Process for removing and isolating solasodine from the aqueous-alcohol extract of fruit containing solasodine glycoside comprising removing the alcohol from said extract, precipitating impurities, precipitating said glycoside, hydrolyzing said precipitated glycoside with an acid-isopropanol mixture, and precipitating solasodine from the hydrolyzate.

30 Claims, No Drawings

PROCESS FOR RECOVERING AND ISOLATING SOLASODINE AND GLYCOSIDES THEREOF

This is a continuation, of application Ser. No. 331,004, filed Feb. 9, 1973 now abandoned.

BACKGROUND OF THE INVENTION

Sapogenins have achieved considerable usefulness as precursors for the preparation of steroid drugs, including sex hormones and cortisone. They are found in certain plant tissues in a combined glycosidal form known as saponins, and are generally removed therefrom and isolated by extraction.

Diosgenin is presently one of the principal sources of steroid drug "raw material" and is, perhaps, the sapogenin most widely used for this purpose. It occurs in glycosidal form in many species of the Liliaceae and Diosoreaceae families, but current commercial production of diosgenin relies primarily on two species of the Dioscoreaceae family Dioscorea mexicana (carbega de negra) and Dioscorea Composita (barbasco), in which the diosgenin is concentrated in the large, fleshy rhizomes, thus permitting yields up to approximately 1% of wet weight. These plants are not well suited for cultivation and require several years before they mature sufficiently to permit a reasonable harvest.

Removal and isolation of sapogenins from the glycosidal form found in certain plants has generally been accomplished by extraction of the fresh (wet) plant tissue with concentrated organic solvents such as benzene or combinations of benzene and concentrated alcohols, followed by acid hydrolysis, further extractions with benzene and in some cases chromatographic adsorption on alumina.

An equally suitable steroid precursor is solasodine which may be readily converted into 16-dehydroprognenolene acetate which is a very convenient percursor to steroid drugs. Solasodine occurs in glycosidal form in the fruit of huapag, a wood perennial of the genus Solanum, which is well suited for cultivation. This species thrives in certain high altitude regions in the tropic zone, for example, near Quito, Ecuador. Under such conditions this species will bear a small crop after two years, a much larger crop after five years, and will continue to bear all year round for many additional years.

The plant referred to herein as huapag is known by this name in the Quito area. In other parts of Ecuador, it is known as "jabon de pobres" and "huevo de tigre". It appears to be identical to one of the types of *Solanum marginatum* L., as described by Dunal (Dunal, M.F., Solanaceae, in de Candolle, Prodomus 13 (1): 1-690, 1852), the huapag being the type showing a spiny calyx.

Glycosides of solasodine are also known to occur in the fruits of several other species of the genus Solanum, particularly in tree Solanum. The plant referred to herein as tree solanum appears not to have been described in the botanical literature. It occurs wild near Archidona, Ecuador in the province of Napo (where it is known as apumpo) and also near Yacuambi, east of Loja, Ecuador, in the province of ZamoraChinchipe. A botanical definition of the tree Solanum follows:

Tree up to 20 meters or more with few to many scattered spines on trunk and main branches, young branches with stellate trichomes; leaves simple, from oval with nearly smooth margins to four or more lobes, nearly glabrous or with many stellate trichomes, blade usually unequal at base, about ¾ as wide as long; flowers 6.0–7.0 cm. across, in clusters, purple fading to white with age, stellate hairs on both surfaces, calyx enlarging in fruit to 3.0–4.0 cm. across and becoming thickened (about 1.0 cm. thick around top of fruit); stamens yellow, tapered, another anther cm., filament 0.3 cm.; fruit single or in clusters (2–5), glabrous, green when mature, globose, 4.0–5.5 cm. in diameter, flesh greenishwhite; seeds numerous, flat, light-brown, about 0.3 cm. long.

Both tree Solanum and huapag are members of the stellate Leptostemonum group. The plants referred to herein as the stellate Leptostemonum group constitute the sub-genus Leptostemonum as defined by MacBride (J. F. MacBride, Flora of Peru, Field Museum of Natural History, Botanical Series, Volume 13, Part 5-B, Nov. 1, 1962) but further limited to exclude species which have only simple trichomes on the leaf petioles.

In glycosides, solasodine is chemically combined with sugars, and the identity and linkage of the sugar portion varies. For example, S. Marginatum is reported to contain solasonine and solamargine, both of which are glycosides of solasodine, but in which the sugar portions differ. In this application, the terms "glycosides" and "glycosides of solasodine" should be understood to mean any glycoside or mixture of glycosides of solasodine.

The difficulties of obtaining solasodine in usably pure form from these plant sources have seriously militated against the commercial development of this source of raw materials for hormones. It is known that glycosides of solasodine can be efficiently extracted from plant sources by extraction with aqueous lowboiling alcohols. However, extracts so obtained contain considerable proportions of other materials extracted from the plant sources along with the desired glycosides. While methods have been described for separating these impurities from the desired glycosides or from solasodine obtained from the glycosides by hydrolysis, such methods are laborious and result in loss of a considerable proportion of the desired steroids.

Furthermore, the hydrolysis step, especially if it be carried out with crude glycosides obtained in a practical extraction of said plants, normally leads to impure solasodine. This can be purified but the purification entails considerable effort and loss of product.

One problem in the hydrolysis of the glycosides of solasodine results from the tendency of these compounds to suffer dehydration to solasodiene under the vigorous conditions normally used for the hydrolysis. This tends to cause both a lowered yield of the desired aglycone and contamination of the solasodine with solasodiene.

Another problem in the hydrolysis of said glycosides to produce solasodine results from the tendency of the aglycone to be contaminated by impurities of unknown structure. One possible source of impurities of unknown structure is impurities in the glycosides used as starting material. All known convenient methods of obtaining said glycosides from natural sources yield products in which the glycoside content is much less than 100%. It is not known whether the impurities contained in glycosides obtained from natural sources are changed chemically in the course of acid hydrolysis used to convert the glycosides to the aglycone, but these impurities or their reaction products, or both, tend to appear as contaminants in the aglycone.

Another possible source of impurities of unknown structure is the decomposition of the glycosides or their hydrolysis products during the hydrolysis step. Besides producing by-products which contaminate the desired aglycone, these reactions cause a loss of yield.

Thus, a variety of impurities may be present in the solasodine resulting from the hydrolysis of crude glycosides thereof. Of all of these impurities, the most important in amount and in tendency to contaminate the product solasodine are those arising from impurities in the crude glycosides as these are normally extracted from plant material. This is true of the glycosides obtained according to the method given in this application, even though the glycosides so obtained are exceptionally pure as compared with those obtained by any convenient method previously disclosed.

SUMMARY OF THE INVENTION

In the process according to the present invention, solasodine can be recovered from the aqueous alcoholic extract of a fruit containing solasodine in glycosidal form by a process which is very simple and efficient and which provides a high yield of high purity product. In the first part of the process, a major portion of the impurities which normally accompany the glycosides of solasodine when so extracted is removed. To remove said impurities, the aqueous alcoholic extract is distilled until essentially all of the alcohol is removed. After said distillation the volume of the aqueous extract is adjusted by the addition of water or by the distillation of water. The resulting precipitate, which consists almost entirely of impurities, is removed by decantation, filtration, or centrifugation. Glycosides of solasodine may then be recovered from the solution by alkalization followed by filtration or centrifugation.

In the second part of the process, said glycosides of solasodine are hydrolyzed and the resulting solasodine is recovered in unusually pure form.

The hydrolysis is carried out by treating the crude glycoside at about the boiling point in a mixture consisting of glycoside, isopropanol, hydrogen chloride, and water. After the hydrolysis is complete, the mixture is brought to a pH of 9 to 10 by addition of concentrated aqueous alkali.

Under these conditions, there is formed a precipitate which consists almost exclusively of solasodine and materials easily soluble in water. The precipitate is separated from the liquids and is washed with water, which leaves essentially pure solasodine.

DETAILED DESCRIPTION OF THE INVENTION

In the part of this invention which refers to the extraction of glycosides from fruit, said fruit is any fruit of the stellate Leptostemonum group. Preferable, said fruit may be that of huapag or of tree Solanum. More preferable, said fruit is that of huapag in such a degree of ripeness that the skin of the fruit shows some yellow area, but such that not more than 90% of the area is yellow. This will be referred to as the yellow-green stage.

Most preferably, said fruit may be the fruit of huapag in the pinton stage. By pinton fruit is meant fruit of such a degree of ripeness that a portion of the outer surface of the fruit amounting to between 5% and 50% of said shows a color of 19 or lower number but none of said surface shows a color of 16 or lower number. Furthermore, the greenest portion of said surface corresponds to a color of 23 or a lower number. The color numbers given here are those of the Farnsworth-Munsell, 100 Hue Test for Color Vision, sold by the Munsel Color Company Inc., 2441 N. Calvert St., Baltimore 18, Maryland.

In the case of tree Solanum, the preferred degree of maturity is also termed pinton, since it is the stage of maturation at which the fruit has a consistency very similar to that of the pinton fruit of huapag. This normally is the ripest fruit found on tree Solanum growing in the Archidona area in the month of December.

A requirement of the alcohol chosen for the above-mentioned extraction is that it be readily distillable from water. Practically, this limits the choice of alcohols to methanol, ethanol, isopropanol, and mixtures thereof. Ethanol and isopropanol are preferred, and isopropanol is most preferred. The relative proportions of alcohol and water may be varied widely, but a proportion of alcohol from about 50% to 90% is preferred.

Before the extraction, the fruit, which may be used either fresh or dried, is cut or broken to facilitate access of the extractant to the interior of the fruit. In cutting or breaking the fruit, care should be exercized to minimize the rupture of the seeds since said rupture tends to release impurities which are difficult to separate from the desired products.

After the extraction, essentially all of the alcohol is removed from the extract by distillation. Said distillation may be carried out at atmospheric pressure, but it is preferred to use reduced pressure such the temperature of the boiling liquid does not exceed about 60°C. After said distillation, the weight of the aqueous extract is adjusted by the addition of water or by further distillation, said further distillation being carried under the same limitations of temperature and pressure as the previous distillation. The minimum weight of the aqueous extract after said adjustment depends upon whether the fruit was dried before extraction. If the fruit has been dried, which appears render the impurities more readily precipitated, said minimum weight is about 0.2 times the wet (as-picked) weight of the fruit extracted. However, if the fruit has not been dried, said minimum weight is about 0.3 times said wet weight. The preferred weight of the aqueous extract after said adjustment is about one-half of said wet weight. Carrying said adjustment to a greater weight appears to bring no advantages but it does entail the inconvenience of handling larger volumes as well as greater loss of glycoside by solubility if said glycosides are subsequently precipitated.

It is preferred to carry out said adjustment of weight at an elevated temperature, preferably about 60°C., for two reasons. First, convenience, because at the completion of the distillation the aqueous extract is at an elevated temperature. Second, because the subsequent filtration of P is somewhat easier if said adjustment is carried out at an elevated temperature.

Said adjustment having been carried out, a precipitate (herein referred to as P) of impurities forms and is separated from the aqueous extract. Said separation may be carried out at elevated temperature, but in the interest of more complete precipitation of impurities it is preferred to carry out said separation at room temperature, preferably after the adjusted aqueous extract has stood for at least an hour at room temperature. Said separation of P may be carried out centrifugation, filtration, or any other convenient means.

The liquid remaining after separation of P contains glycosides in solution. Said glycosides may be recovered from said liquid by means known in the art, for example by addition of aqueous ammonia or aqueous sodium hydroxide, which causes said glycosides to precipitate. Alternatively said liquid may be used directly as a source of crude glycosides.

Various criteria may be applied to demonstrate that the steps of adjustment of the weight of the aqueous extract and removal of P do, in fact, serve to increase the purity of the extracted glycosides. For example the quantity of glycosides in the extract before removal of P may be shown to be substantially equal to the quantity of glycosides remaining after removal of P. This criterion is applied in examples I-A and V-A.

Another criterion is to show that the material described as impurities is not, in fact, glycosides of solasodine, on the basis of melting behavior, as is done in example I-A and VIII-A.

A further criterion is to compare the behavior on hydrolysis of the crude glycosides from which P has been separated with the behavior of crude glycosides prepared similarly with the exception that P has not been removed or has been added back. This criterion is applied in example VI and the experiments described immediately thereafter.

A still further criterion is to compare the color, consistency, and volume of the precipitate, P, obtained in a given experiment with that obtained in another experiment w where other criteria were applied. This criterion is applied in examples V-A, VII, XIII, XIV, XV, XVI, and XVII.

In the part of this invention which refers to the hydrolysis of glycosides, said glycosides may have their origin in the fruit of any plant of the genus Solanum. It is preferred to use glycosides originating in fruit of the stellate Leptostemonum group, and more preferred to use glycosides originating in fruit selected from the group consisting of the fruit of tree Solanum in the pinton stage and the fruit of huapag in the yellow-green stage. Most preferred is the fruit of huapag in the pinton stage.

In the hydrolysis of the glycosides of solasodine, specific proportions of the crude glycoside, isopropanol, hydrogen chloride and water are used. After the hydrolysis is complete, the mixture is brought to a pH between 9 and 10 by the addition of concentrated aqueous alkali. This produces a precipitate which contains essentially all of the aglycone. This precipitate is easily separated from the supernatant liquid by filtration or centrifugation. Surprisingly, it has been found that essentially all of the impurities in the precipitate so produced are easily removed by washing with water, leaving the desired solasodine in a very good state of purity.

The concentrated aqueous alkali is sodium or potassium hydroxide or carbonate. The minimum operable concentration is about 20% sodium hydroxide (weight/weight) or an equivalent (in neutralizing power) solution of any of the other abovementioned bases. A concentration twice as great as this is preferred and hydroxides are preferred over carbonates. Most preferred is 40% aqueous sodium hydroxide.

In the foregoing, reference has been made to the pH of the mixture after hydrolysis and alkalization. It has been found that measurement of this pH with a typical pH meter is impractical, in that it is difficult if not impossible to obtain a stable reading of the pH. It has been found much more satisfactory to measure this pH with an indicator paper such as "Ederol" Universalindikator pH 1–13 which is sold by J. C. Binzer Vertriebs, GMBH, Harzfeld Eder, Germany, in accord with the instructions provided with the paper. The package thus identified contains two types of paper; the type marked pH 6–13 is used. In all cases where reference is made in this specifications to the pH of the alkalized hydrolysis mixture, the pH as measured with Ederol Universalindikator paper is to be understood.

In the course of the addition of the concentrated aqueous alkali, it is observed that the viscosity of the hydrolysis mixture decreases and the color of the liquid darkens. These changes signal the approach to the desired pH range, but the determination of the attainment of the desired pH is desirably done with Ederol Universalindikator paper, as described.

Heating glycosides of solasodine with acidified aqueous alcohol to effect their hydrolysis is known. What is novel in the hydrolysis according to this invention is the selection of a particular range of proportions in the hydrolysis medium and the choice of one alcohol, isopropanol, combined with the subsequent alkalization of the hydrolysis mixture in a specified manner, all of which results in the production of a precipitate, which consists of the desired aglycone mixed with impurities which are easily removed by washing with water.

As is known, the use of an elevated temperature is necessary to cause the hydrolysis of the glycosides of the present invention to proceed at a reasonable rate. The temperature chosen in the examples given below is that required for reflux of the solvent mixture chosen at a pressure of about 540 mm. of mercury, that being the normal atmospheric pressure in Quito, Ecuador, the site where the experimental work upon which this application is based was carried out. However, the only significant effect of moderate changes in the temperature of the hydrolysis would be to cause moderate changes in the rate of the hydrolysis. Thus, the hydrolyses illustrated in the examples would occur more rapidly under reflux at sea level. If desired, it would be feasible to carry out said hydrolyses under mildly superatmospheric pressure in even shorter times.

In the examples which follow, the time of heating to effect hydrolysis is 3 hours, that being the length of time required for essentially complete hydrolysis under the conditions described in the examples. Should it be desired to determine the required length of time for hydrolysis, for example, under conditions differing markedly from those described in the examples, this can be done by running a series of test hydrolyses for varying lengths of time and adopting the least length of time which gives a satisfactory yield. Normally, a length of time should be chosen such that a longer time leads to no significant increase in yield.

In the examples which follow, the hydrolysis mixtures are cooled before they are neutralized. Nevertheless, alkalization at higher or lower temperature is perfectly feasible. Of course, considerable heat is evolved in the alkalization. Thus, it may be necessary to take steps to a avoid the loss of isopropanol. This may take the form of external cooling or the use of a reflux condenser. However, because excessive temperatures during the alkalization may lead to some decomposition of the solasodine, it is preferred to carry out the alkalization at a temperature not greatly in excess of room temperature.

While the rate at which the aqueous alkali is added is not important, it is desirable to agitate the mixture well as the alkali is added, in order to avoid inadvertently exceeding the specifiec pH range. However, the addition of a moderate excess of alkali beyond that required to attain the specified pH range is not serious, since the pH may be brought back to the specified range by the addition of hydrochloric acid. Before the alkalization, the aglycone is present as the hydrochloride. Alkalization as described causes the free aglycone to precipitate.

It is desirable that the centrifugation or filtration be carried out at a temperature not significantly above room temperature to avoid excessive loss of the aglycone through solubility of the aglycone in the liquid. Furthermore, permitting the alkalized mixture to stand before separation of the solid precipitate is desirable in that it leads to more complete precipitation of the aglycone.

For the operation of the hydrolysis according to the process of this invention, it has been found necessary that the composition of the hydrolysis mixture be as follows (all quantities expressed as parts by weight):

| | |
|---|---|
| glycosides | up to 16 |
| isopropanol | 55 to 72 |
| hydrogen chloride | 4 to 8 |
| water | to make 100 | preferred and most preferred porportions are as follows:

| | preferred | most preferred |
|---|---|---|
| glycosides | 6 – 16 | 10 – 13 |
| isopropanol | 60 – 65 | |
| hydrogen chloride | 5 – 7 | 6 |

Substances in the crude glycoside other than water and actual glycosides are not considered in calculating the composition of the hydrolysis mixture.

Two factors have a bearing on the choice of the proportions of water and isopropanol in the solvent. The lower the concentration of water used, the more cleanly the hydrolysis reaction runs, the lower limit of the water concentration being the practical one of a hydrolysis mixture in which the sole source of water is that contained in the concentrated hydrochloric acid used to provide the hydrogen chloride. On the other hand, the viscosity of the hydrolysis mixture is increased when small amounts of water are used, and it is the high viscosity which sets the upper limit of the concentration of glycoside which can practically be used. Thus, it is necessary to strike a compromise in the choise of water concentration.

One source of water in the hydrolysis mixture may be moisture in the glycoside. This material, commonly obtained as a filter cake wet with water, need not be dried before it is put into the hydrolysis mixture except insofar as is necessary to avoid raising the water content of the hydrolysis mixture beyond the desired level.

The hydrolysis according to the process of this invention is principally directed to the hydrolysis of crude glycosides, that is, those which are in such an impure condition as results from a fairly simple extraction of the glycoside from plant material. In the hydrolysis of purified glycosides the separation of the aglycone from by-products tends to be relatively simple, as that the special features of this invention probably would not be needed.

The hydrolysis of this invention works especially well with crude glycosides such as are produced by the method of this invention, where the purity of the glycoside is about 90% on the basis of the dry weight. However, it also functions satisfactorily with starting materials of higher or lower purity, the purity of the final product solasodine being adversely affected if the crude glycoside contains excessive amounts of impurities.

EXAMPLE I

A. The fruit of huapag is picked in the pinton stage. One kg. of fruit is used. Each fruit is divided into quarters by two mutually perpendicular cuts along the axis of the fruit. The fruit is then dried in an oven at 60°C. until brittle enough to grind easily. The fruit is then ground in a simple grooved-disc mill set so as to barely avoid fracturing the seeds. The weight of the ground fruit is 270 g. The solids content of the ground fruit is 94% based on weight loss at 100°C.

For the extraction the ground fruit is placed in a two liter erlenmeyer flask and 810 ml. of aqueous isopropanol (77% isopropanol by volume) is added. The flask is stoppered and extraction is carried out at room temperature for 2 hours with alternating 5 minute periods of vigorous manual agitation and rest. The extraction mixture is drained on filter paper in a conical funnel and the solids are returned to the erlenmeyer flask. For a second extraction a further portion (540 ml.) of aqueous isopropanol is added and the alternate agitation and rest is repeated except that the period in one hour instead of two. The liquids are again drained as before. Then, a third extraction, identical to the second, is carried out. All three filtrates are combined and the combined liquids are analyzed for glycoside content, the result being 16.7 g. of total glycosides.

The determination of glycosides of solasodine, in all cases referred to in this application, is carried out according to the method of Lewis and Liljegren (Phytochemistry, 9 2194 (1970) except that the samples (in aqueous isopropanol) are evaporated to dryness before the analysis, and are then dissolved in the phosphoric acid solution before the formaldehyde solution is added.

The combined liquids are fed slowly into a one-liter rotary evaporator heated with a water bath at 60°–70°C. The initial pressure is about 150 mm. of mercury, and this is gradually reduced to 50 mm. by which time the distillate is essentially pure water. The aqueous residue is not allowed to cool, but its weight is adjusted to 510 g. by the addition of water heated to 60° – 70°C. The addition of the water is made over a 2 minute period, while the mixture is being stirred. A precipitate forms immediately. The mixture is then allowed to stand for 4 hours, during which time it cools to approximately room temperature.

The supernatant liquid is then decanted through medium filter paper and finally the precipitate (P) is transferred to the filter paper. P is a finely divided but easily filtered material. Its color is olive-drab. After drying at 100°C P weighs 1.9 g. This material begins to melt at about 160°C., but is not yet completely melted at 230°C.

The filtrate is placed in a one liter round-bottom flask fitted with a reflux condenser and is then heated to 80°C. It is maintained at this temperature and agitated magnetically while 15 ml. of 25% aqueous ammonia is added, and agitation at 80°C. is continued for one hour more. The mixture is immediately filtered through medium paper and the filtrate is discarded. It has a pH between 9 and 10 and is free of glycosides as indicated by the Dragendorff test.

The filter cake, still on the filter paper, is pressed between absorbent papers to remove as much of the liquid as possible. Then, it is dried at 60°C. to a final weight of 25.7 g. Further drying at 100°C gives a weight loss of 27.7%. Analysis of a sample of the 25.7 g. cake shows that it contains 16.7 g. of glycosides and indicates a negligible loss of glycosides in the purification and isolation.

In an analogous experiment in which the cooling, waiting, and filtration of P was omitted, and in which the glycosides were precipitated as in Example I-A, it was impossible to filter the precipitated glycosides.

B. In a one-liter ground-buttom flask are placed 46 g. of damp crude glycoside (prepared as described in part A of this example), 138 g. isopropanol, 37 g. hydrochloric acid (37.6% HCl), and 9 g. tap water. The flask is equipped with a reflux condenser and magnetic agitation and is heated to reflux in a water bath for 3 hours. At the end of this time the contents is a light brown suspension, which is allowed to cool to room temperature over a period of 2 hours. There is then added 40% (weight) sodium hydroxide in water. The sodium hydroxide is added in 5 ml. increments at first, and later dropwise. Between additions, the mixture is swirled vigorously by hand for one to two minutes. At about pH 9 the viscosity oof the mixture decreases noticeably, the color deepens and the formation of a second liquid phase becomes apparent. Addition of alkali is stopped at an pH of about 9.5 to 10, by which time there are observable a considerable separation of the liquid into two phases and the formation of a precipitate. The total amount of sodium hydroxide solution added in 29 ml. The mixture is allowed to stand 1½ hr. at room temperature and then is filtered by gravity through medium paper. The precipitate is dried by pressing between absorbent papers.

The filtrate consists of two layers. The upper layer is brown and appears to contain the major portion of the isopropanol as well as a very small amount of solasodine, in addition to impurities. The lower layer is dark brown and appears to contain water, sodium chloride and impurities. The entire filtrate is discarded.

The damp participate is agitated with one liter of tap water while aqueous hydrochloric acid is added until the pH is between 6 and 7. It is then allowed to stand overnight. Then, the mixture is filtered by gravity through medium paper and the precipitate is pressed between absorbent papers. The precipitate is dried in an oven at 60°C for 12 hours.

The dry weight of the precipitate is 14 g., and it melts 196° – 19 °C. The solasodiene content is 1.25%, as determined by the method of Bragins and Pervacheva (L. N. Bragina and T. D. Pervacheva, Med. Prom. SSSR, 16 No. 11, 36–9 (1962). This method is used for all solasodiene analysis referred to in this application. The precipitate is estimated to contain 97% solasodine on the following basis: Pure solasodine is reported to melt 200° – 202°C. An early, less pure sample produced here melted 191° – 197°C. and contained 95% solasodine as determined by the method of Birner (J. Birner, J. Pharm Sci, 58, 258 (1969). Birner's method, as reported in the abovementioned reference, is designed for determination of steroid bases in fruits. However, his Procedure A is directly applicable for the assay of solasodine in a dry powder, and is used as such in this work.

By interpolation, based on mid-points of melting ranges, the above estimate of 97% purity is arrived at. This is the method of solasodine assay used throughout this application. The 46 g. of crude glycoside taken for this example contains 30 g. of glycosides of solasodine. Thus, the 14 g. of product represents a 98% yield in the hydrolysis step.

In the hydrolysis mixture of this example, the isopropanol constitutes 60% by weight, hydrogen chloride constitutes 6%, the glycosides constitute 13% of the weight.

EXAMPLES II, III

Examples II and III are hydrolyses carried out as described for example I-B, the only differences being in the proportions of the materials used in the hydrolysis mixture. These proportions and the results of the examples are given in Table I. The corresponding data for example I-B are repeated for comparison.

EXAMPLE IV

The procedure of example I-B is followed, except that 550 g. of damp crude glycoside is used, prepared as in example I-A, but dried more thoroughly at 60°C., and the glycosidecontent is 458 g., amounting to 11.8% of the weight of the hydrolysis mixture. The volume of water used to wash the precipitate is 19 liters. The product weighs 205 g., melts at 197°–199°C., and has a diene content of 0.67%. This is a 98% yield on the basis of the starting glycosides. Data on this example are included in Table I.

EXAMPLE V

This procedure is identical to that used for example I, with the following exceptions:

A. The fruit used is 1.24 kg. of the fruit of tree Solanum, of such a degree of ripeness as to have a consistency similar to that of the pinton fruit of huapag. Its color is green. After grinding, the fruit weighs 220 g. and its solids content is 95.5%. The glycoside content of the combined extracts is 11.8 g. The weight of the aqueous extract is adjusted to 440 g. The glycosides, after drying at 60°C. weigh 17 g. Analysis indicates a glycoside content of 11.7 g., and the drying at 100°C gives a weight loss of 19%. Thus, impurities contained in the glycosides amount to 12% of the 17 g.

The precipitate P is of similar color and consistency to that obtained in example I-A. Its volume appears to be in proportion to the quantity of fruit processed.

B. In the hydrolysis, all 17 g. of damp crude glycosides prepared in example V-A are used. A 500 ml. flask is used and percentages of reagents are as given in Table I, as are product data. For alkalization 11.5 ml. of 40% NaOH are required. For washing the precipitate, 500 ml. of water is used. Data are given in Table I.

EXAMPLE VI

This example is carried out in a manner identical to example I, with the following exceptions:

Each fruit is chopped in a random manner into about 16 pieces. The fruit is not dried. The extraction solvent is aqueous isopropanol (82% by volume). Four extractions are carried out, each with 500 ml. of extraction solvent. Each extraction is for one hour. The aqueous extract, after distillation of the isopropanol is diluted to a volume of 600 ml. In the precipitation of the glycosides, 21 ml. of 25% aqueous ammonia is used. For purposes of making up the hydrolysis solvent, it is assumed that the damp crude glycoside cake contains 14 g. of glycosides and 1.5 g. of impurities, the remainder being water. In the hydrolysis a 500 ml. flask. is used. The composition of the hydrolysis mixture is given in Table I. The precipitate is washed with 500 ml. of water, without the addition of acid. Data are given in Table I.

The precipitate P is of similar color and consistency to that obtained in example I-A. Its volume appears to be in proportion to the quantity of fruit processed.

In an analogous experiment in which the impurities precipitated from the aqueous extract were mixed back in with the glycosides after isolation of the glycosides, the final product of the hydrolysis and isolation did not begin to melt up to a temperature of 210°C. Thus, if the final product contained solasodine, it was highly impure.

In another analogous experiment in which the weight of the aqueous extract was adjusted in the fashion of example VI, but the cooling, waiting, and filtration to remove P were omitted, the final product of the hydrolysis did not begin to melt up to 210°C. Thus, if the final product containend solanodine, it was highly impure.

EXAMPLE VII

Both the extraction and the hydrolysis are carried out in a manner identical to that of Example VI, except that aqueous ethanol (90% by volume) is used in place of aqueous isopropanol in the extraction. Data are given in Table I.

The precipitate P is of similar color and consistency to that obtained in example I-A. Its volume appears to be in proportion to the quantity of fruit processed.

EXAMPLE VIII

The fruit of huapag is picked at the stage where about 80–90% of the surface is yellow. Eight kg. of fruit is used, cut into slices about 7 mm. thick, the plane of slicing being chosen at random with respect to the axis of the fruit. The extractant is 82% aqueous isopropanol, and 6 liters is used for each of three extractions. For each extraction, the mixture of fruit and solvent is shaken mechanically in a 20 liter bottle for one hour. Then, the mixture is strained through a sieve of such size as just to retain the seeds. The material retained on the sieve is then returned to the bottle for the next extraction. Finally, the strained material from all three extractions is combined and permitted to settle for 2½ hours. The supernatant liquid is decanted through medium filter paper and then the sediment is drained and pressed on the same paper. The volume of the filtrate is 20.5 liters.

One-eight of the filtrate is taken for further treatment as described in example I-A, with the following exceptions.

The adjusted weight of the aqueous residue is 400 g. P when dried, weighs 1.1 g. and begins to melt at 180°C., but is not yet completely melted at 230°C., at which temperature darkening of color begins. P, when wet has similar color, consistency, and volume to that obtained in example I-A.

Ammonia (25%, 13.7 ml.) is used to precipitate the glycosides and the dried product weighs 22.0 g.

Data on hydrolysis and product are given in Table I; further difference from example I-B are as follows:

A one-half liter flask is used. The volume of sodium hydroxide solution is 14.4 ml. The precipitate is washed with 700 ml. of water, whose pH is between 6 and 7 without the addition of hydrochloric acid.

EXAMPLES IX, X, XI

These are hydrolyses carried out as described in example I-B but using a different batch of glycosides and on a 20% smaller scale.

Conditions are as described for example I-B except that the aqueous alkali is varied as indicated in Table II, with the results that are given in the Table.

TABLE II

| Example | aqueous alkali | PRODUCT (SOLASODINE) | | |
|---------|---------------|---------|---------|---------|
|         |               | yield % | m.r.(°C) | diene content |
| IX      | NaOH (40%)    | 98      | 197–199 | 0.9%    |
| X       | NaOH (20%)    | 70      | 192–199 | 1.0%    |
| XI      | KOH (56%)     | 91      | 196–200 | 0.9%    |

In a further experiment using 10% aqueous sodium hydroxide, the product weighed 3.7 g., began to sublime at 210°C., and began to melt at 219°C. Thus, if the product contained solasodine, it was highly impure.

EXAMPLE XII

This is a hydrolysis carried out on 1/2 the scale of example I-B with different proportions in the hydrolysis mixture. Data on the hydrolysis mixture and product are given in Table I.

EXAMPLE XIII

This example is identical with example I, with the following exceptions:

The scale is 1/2 that of example I, and the distillation to remove isopropanol is carried out at atmospheric pressure (approx. 540 mm Mg) which requires a final temperature in the bath (oil) of 98°–100°C. The product differs from that of example I only in that the yield is reduced to 81.5%.

The yield is calculated as moles of solasodine in the final product divided by moles of glycosides in the aqueous alcoholic extract.

The precipitate P is of similar color and consistency to that obtained in example I-A. Its volume appears to be in proportion to the quantity of fruit processed.

EXAMPLES XIV, XV, XVI, XVII

These are examples designed to define the lower limit of the adjusted weight of the aqueous extract in terms of the formation of a filtratable precipitate P of impurities. Examples XIV and XV are nalogs of example I-A. Examples XVI and XVII are analogs of example VIII-A. Data are given in Table III. "Adjusted weight" in the adjusted weight of the aqueous extract as a fraction of the wet weight of the fruit extracted.

TABLE III

| Example | "Adjusted weight" | Nature of Precipitate (P) |
|---------|-------------------|---------------------------|
| XIV     | 0.19              | Stable, very compact, easily centrifuged |

TABLE III-continued

| Example | "Adjusted weight" | Nature of Precipitate (P) | | |
|---|---|---|---|---|
| XV | 0.23 | stable, | | easily centrifuged |
| XVI | 0.29 | stable, | compact | centrifuged |
| XVII | 0.38 | stable, | very compact | centrifuged |

All precipitates (P) are of similar color, consistency and volume to that obtained in example I-A.

In an experiment analogous to example XIV, in which the adjusted weight was 0.13, no precipitate was formed. In another experiment analogous to example XVI, in which the adjusted weight was 0.19, a precipitate formed temporarily but redissolved.

TABLE I

| Example | Materials in Hydrolysis Mixture (%) | | | weight (g.) | Product (solasodine) | | yield |
|---|---|---|---|---|---|---|---|
| | isopropanol | HCL | glycosides | | m.r.(°C) | diene content (%) | (g) |
| I B | 60 | 6 | 13 | 14.0 | 196–198 | 1.25 | 98 |
| II | 65 | 6 | 13 | 14.1 | 196–198 | 1.22 | 99 |
| III | 55 | 6 | 13 | 13.2 | 196–198 | 1.29 | 93 |
| IV | 60 | 6 | 11.9 | 2.05 | 197–199 | 0.67 | 98 |
| V B | 60 | 6 | 13 | 5.4 | 198–200 | 1.20 | 96 |
| VI | 60 | 6 | 13 | 5.2 | 198–199 | 0.98 | — |
| VII | 60 | 6 | 13 | 5.1 | 198–199 | 1.12 | — |
| VIII | 60 | 6 | 10.6 | 5.7 | 196.5–199 | 1.1 | — |
| XII | 67 | 7.6 | 6.2 | | 197–199 | 1.0 | 89 |

I claim:

1. A process of obtaining a solution of glycosides of solasodine comprising:
   a. extracting in either the fresh or dried state the cut or broken fruit of a plant of the stellate Leptostemonum group with a mixture of water and an alcohol selected from the group consisting of methanol, ethanol, isopropanol, and mixtures thereof;
   b. removing substantially all of the alcohol from the resulting aqueous-alcoholic extract by distillation;
   c. adjusting the weight of the resulting aqueous extract so that the weight of the adjusted aqueous extract is at least about 0.2, if said fruit was dried before said extraction, or about 0.3, if said fuit was not dried before extraction, times the wet weight of said fruit; and
   d. removing the precipitate from said adjusted aqueous extract.

2. The process according to claim 1, wherein the weight of the adjusted aqueous extract is at least about 0.4 times the wet weight of the fruit extracted.

3. The process according to claim 1, wherein the alcohol is isopropanol.

4. The process according to claim 2, wherein the alcohol is isopropanol.

5. The process according to claim 1, wherein the fruit is selected from the group consisting of the fruit of tree Solanum in the pinton stage and the fruit of huapag in the yellow-green stage.

6. The process according to claim 2, wherein the fruit is selected from the group consisting of the fruit of tree Solanum in the pinton stage and the fruit of huapag in the yellow-green stage.

7. The process according to claim 5, wherein the alcohol is isopropanol

8. The process according to claim 6, wherein the alcohol is isopropanol

9. The process according to claim 8, wherein the fruit is that of huapag in the pinton stage.

10. A process for recovering and isolating solasodine comprising:
    a. extracting in either the fresh or dried state the cut or broken fruit of a plant of the stellate Leptostemonum group with a mixture of water and alcohol selected from the group consisting of methanol, ethanol, isopropanol, and mixtures thereof;
    b. removing substantially all of the alcohol from the resulting aqueous-alcoholic extract by distillation;
    c. adjusting the weight of the resulting aqueous extract so that the weight of the adjusted aqueous extract is not less than about 0.2, if said fruit was dried before extraction, or about 0.3, if said fruit was not dried before extraction, times the wet weight of said fruit;
    d. removing the precipitated impurities from said adjusted aqueous extract;
    e. precipitating crude glycosides from said adjusted aqueous extract sans impurities by alkalization;
    f. removing the precipitated crude glycosides;
    g. heating a mixture consisting essentially of said crude glycosides, up to 16 parts by weight, isopropanol about 55 to 72 parts by weight, hydrogen chloride 4 to 8 parts by weight, and water to make 100 parts by weight for a length of time sufficient to bring about substantially complete hydrolysis of the glycosides;
    h. adding to said mixture concentrated aqueous alkali selected from the group consisting of sodium hydroxide, potassium hydroxide, sodium carbonate, and potassium carbonate until the pH of said mixture is between about 9 and about 10;
    i. separating the precipitated solasodine from said alkalized mixture;
    j. washing said precipitated solasodine with water.

11. The process according to claim 10, wherein:
    a. the fruit is selected from the group consisting of the fruit of tree Solanum in the pinton stage and the fruit of huapag in the yellow-green stage;
    b. the extraction is made with aqueous isopropanol;
    c. the weight of the adjusted aqueous extract is at least about 0.4 times the wet weight of the fruit extracted;
    d. the hydrolysis mixture consists essentially of crude glycosides, 10 to 13 parts by weight, isopropanol 60 to 65 parts by weight, hydrogen chloride 5 to 7 parts by weight, and water to make 100 parts, and
e. the concentrated aqueous alkali is 40% sodium hydroxide.

12. A process of obtaining solasodine by the hydrolysis of crude glycosides obtained from the fruit of a member of the genus Solanum comprising:
    a. heating a mixture consisting essentially of crude glycosides, up to 16 parts by weight, isopropanol 55 to 72 parts by weight, hydrogen chloride, 4 to 8 parts by weight, and water to make 100 parts by weight for a length of time sufficient to bring about substantially complete hydrolysis of the glycosides;
    b. adding to said mixture concentrated aqueous alkali selected from the group consisting of sodium hydroxide, potassium hydroxide, sodium carbonate, and potassium carbonate until the pH of said mixture is between about 9 and about 10;
    c. separating the precipitated solasodine from said alkalized mixture;
    d. washing the separated solasodine with water.

13. The process according to claim 12, wherein the hydrolysis mixture consists essentially of crude glycosides, 6 to 16 parts by weight, isopropanol 60 to 65 parts by weight, hydrogen chloride, 5 to 7 parts by weight, and water to make 100 parts, and the concentrated aqueous alkali is selected from the group consisting of sodium and potassium hydroxides.

14. The process according to claim 13, wherein the fruit is of a plant of the stellate Leptostemonum group.

15. The process according to claim 13, wherein the fruit is of a plant of the stellate Leptostemonum group.

16. The process according to claim 12, wherein the fruit is selected from the group consisting of the fruit of tree Solanum in the pinton stage and the fruit of huapag in the yellow-green stage.

17. The process according to claim 13, wherein the fruit is selected from the group consisting of the fruit of tree-solanum in the pinton stage and the fruit of huapag in the yellow-green stage.

18. The process according to claim 12, wherein the fruit is that of huapag in the pinton stage.

19. A process for hydrolyzing crude glycosides, obtained from the fruit of a member of the genus Solanum, to produce a slurry of solasodine, the process comprising heating a mixture consisting essentially of crude glycosides, up to 16 parts by weight, isopropanol, 55 to 72 parts by weight, hydrogen chloride, 4 to 8 parts by weight, and water to make 100 parts by weight for a length of time sufficient to bring about substantially complete hydrolysis of the glycosides, and adding to said mixture concentrated aqueous alkali selected from the group consisting of sodium hydroxide, potassium hydroxide, sodium carbonate, and potassium carbonate until the pH of said mixture is between about 9 and about 10.

20. The process according to claim 19, wherein the hydrolysis mixture consists essentially of crude glycosides, 6 to 16 parts by weight, isopropanol, 60 to 65 parts by weight, hydrogen chloride, 5 to 7 parts by weight, and water to make 100 parts, and the concentrated alakali is selected from the group consisting of sodium and potassium hydroxides.

21. The process according to claim 19, wherein the fruit is of a plant of the stellate Leptostemonum group.

22. The process according to claim 20, wherein the fruit is of a plant of the stellate Leptostemonum group.

23. The process according to claim 19, wherein the fruit is selected from the group consisting of the fruit of the tree Solanum in the pinton stage and the fruit of huapag in the yellow-green stage.

24. The process according to claim 20, wherein the fruit is selected from the group consisting of the fruit of the tree Solanum in the pinton stage and the fruit of huapag in the yellow-green stage.

25. Product produced by the process of claim 19.
26. Product produced by the process of claim 20.
27. Product produced by the process of claim 21.
28. Product produced by the process of claim 22.
29. Product produced by the process of claim 23.
30. Product produced by the process of claim 24.

* * * * *